United States Patent [19]

Morel et al.

[11] 4,204,842
[45] May 27, 1980

[54] PROCESS FOR CONVERTING BIODEGRADABLE WASTES INTO INDUSTRIAL GASES

[76] Inventors: Pierre Morel, 57, avenue Sainte Marie, Saint-Mande, Vel de Marne; Yasmine Ortega, 19 bis, rue Martin Basse, Caluire; Claudette Jullien; Antonin Jullien, both of 1, rue Henri Gorjus, Lyons 4eme, all of France

[21] Appl. No.: 2,451

[22] Filed: Jan. 10, 1979

Related U.S. Application Data

[63] Continuation of Ser. No. 783,476, Mar. 31, 1977, abandoned.

[30] Foreign Application Priority Data

Apr. 1, 1976 [FR] France .............................. 76 10364
Feb. 17, 1977 [FR] France .............................. 77 05174

[51] Int. Cl.² .................................................. C02C 1/14
[52] U.S. Cl. .................................... 48/197 A; 48/111; 48/209; 71/10; 210/16; 435/167
[58] Field of Search ..................... 48/197 A, 209, 111, 48/197 R; 195/27, 33, 104, 107; 210/2, 6, 11, 16; 71/8, 9, 10, 12

[56] References Cited

U.S. PATENT DOCUMENTS

| | | | |
|---|---|---|---|
| 3,314,765 | 4/1967 | Abson et al. | 71/9 |
| 3,711,392 | 1/1973 | Metzger | 195/33 |
| 3,756,784 | 9/1973 | Pittwood | 71/8 |
| 3,973,923 | 8/1976 | Staege et al. | 48/197 R |
| 4,040,953 | 8/1977 | Ort | 48/197 A |

*Primary Examiner*—S. Leon Bashore
*Assistant Examiner*—George C. Yeung
*Attorney, Agent, or Firm*—Karl F. Ross

[57] ABSTRACT

Biodegradable organic wastes are crushed and then fed to a first cell A of a treatment unit in which they are mixed with liquid recirculated from the discharge end of that unit to form a sludge. After oxygenation in cell A, and following the establishment of an anaerobic atmosphere in that cell by the introduction of carbon dioxide, part of the sludge passes by gravity into a lower-level second cell B for prefermentation with evolution of carbon dioxide. Subsequently, part of the contents of cell B is transferred — again by gravity — to a third cell C, at a still lower level, where fermentation with generation of methane takes place. The methane production is continued thereafter in a fourth cell D at the lowest level, the latter containing a potash solution in which the accompanying carbon dioxide is dissolved while the methane is recovered. The recirculation of liquid from cell D to cell A not only supplies methane-producing bacteria to the incoming sludge but also maintains the latter at a pH of 7 or higher.

11 Claims, 3 Drawing Figures

PROCESS FOR CONVERTING BIODEGRADABLE WASTES INTO INDUSTRIAL GASES

This is a continuation of application Ser. No. 783,476, filed 31 Mar. 1977, now abandoned.

FIELD OF THE INVENTION

The present invention relates to a recycling process for refuse, household-type garbage, and other organic biodegradable wastes by means of a treatment enabling industrial production of a synthetic gas whose composition and production are controlled.

BACKGROUND OF THE INVENTION

The collection and disposal of household-type garbage present various important problems. There is, on the one hand, nuisance and pollution and, on the other, waste of raw materials which are destroyed by conventional techniques.

Two methods are currently practiced. In one, household-type garbage is spread in layers 2.50 m thick and covered up with earth; in the other method, it is incinerated.

The first solution causes underground seepage whose composition and spread are not controlled, which represents a danger for the water table and streams.

The second solution presents the inconvenience of producing ashes whose volume is of the order of 30 to 40% of the burned materials. These ashes can be reused only with difficulty and their destruction therefore presents problems. This destruction can be effected only by burial in the ground, whereupon the ground becomes unsuitable either for agriculture or for construction. In addition, the total amount of methane gas used both in industry and in the home comes at the present time from the exploitation of deposits of natural gas. Depending on the location of the deposits, the composition of natural gases varies. Some gases, such as that of LACQ (a site in France), contain constituents which must be entirely eliminated. This operation is costly and heavily influences the sales price. Gas from LACQ, as used, has a calorific power of 9,960 Kcal/m$^3$. Other gases, such as that of Groninger (in the Netherlands), have noncombustible constituents such as carbon dioxide and nitrogen. These two constituents are not eliminated so as not to increase production cost, but their presence influences unfavorably the calorific power which is of the order of 8,400 kcal/m$^3$. Other gases, such as that of HASSI R'MEL (a site in ALGERIA), have an ideal composition which, besides the fact that they do not require prior treatment, confers to them a high calorific power of the order of 10,700 kcal/m$^3$. Cases like the latter are, however, very rare.

OBJECTS OF THE INVENTION

An object of our invention is to produce a gas with a strong methane content, therefore possessing good calorific power, from a raw material which is worthless. The production of such a gas could be used in oil refineries where heavy oil is used at present as fuel in the refining process. It is to be noted that half of the production of heavy fuel oil is at present utilized in this manner. Utilization of gas allows therefore to economize on heavy fuel and to utilize the saved portion for other purposes.

Another object of our invention is to obtain a new source of energy while insuring collection and destruction of household-type garbage and other refuse at low cost. A related object is to provide a process for so gathering and treating household-type garbage as to obtain by fermentation a gas mixture containing especially methane and hydrogen.

SUMMARY OF THE INVENTION

Pursuant to our invention prefermentation and fermentation phases are effected in cells equipped in such a manner as to control the temperature as well as anaerobiosis. These cells include, furthermore, means to bring in additional substratum in order to resupply themselves with methane-producing bacteria when necessary.

We prefer to mix household-type garbage with other biodegradable organic materials, notably sewer sludge and fecal matter. In a particularly profitable mode of realization of the invention, the crushing of household-type garbage is done at the level of residential or industrial sites by a machine which, while including a crusher connected to a retrieval tank for the waste waters of that site, is also equipped with means to control the activation of the discharge of the waste waters contained in the tank when the crusher is started. The machine is connected also to the sewer inlet pipe so that the refuse and the fecal matter are channeled by the same duct to a main collector and then to a filtering plant, immediately in front of which decanting tanks have been installed in order to allow the separation of:

household-type garbage, fecal matter, sewer sludge, and other biodegradable materials such as paper, cotton fabrics, etc. which remain at the bottom of the tanks by virtue of their respective densities, waste waters and detergents, which are sent on to the filtering plant, the biodegradable materials being then mixed together before being spread in the cells.

This procedure eliminates the collection of household-type garbage as normally practiced, municipal dumpings, as well as incineration plants.

In a preferred mode of realization of this process, the various phases of prefermentation and fermentation with the aid of methane-producing bacteria take place in at least three different cells located directly one on top of the other, the cell in which the first phase takes place being the highest, in order to allow the migration of the materials by gravity from one cell to another one adjacent thereto.

The advantage of this measure resides in the moving of the sludge simply by gravity.

Hence, it is possible to use as a carrier gas the gas produced in the cells where the prefermentation and fermentation phases caused by methane-producing bacteria are taking place.

Indeed, if the cells were located on a common level, an input of outside, industrial carbon dioxide gas would be needed to effect the transfer of the sludge from one cell to the next. However, such practice would adversely affect the gas production since it would induce a decrease in the percentage of produced methane.

In the present case, it is not necessary to provide such an input of carbon dioxide gas. This confers functional autonomy to the system.

The gas mixture contains a large part of methane and a small amount of carbon dioxide. The separation of these two gases is effected in a very simple way, by dissolving the carbon dioxide in a supersaturated solution of potash KOH. After the carbon dioxide has been dissolved, there remains a gas containing 99.5% methane and 0.5% of other constituents such as nitrogen.

This gas has a very significant calorific power of the order of 9,600 kcal/m$^3$. It is of course possible to increase this calorific power so as to bring it up to values ranging from 12,000 to 13,000 kcal/m$^3$ by adding hydrocarbons to it such as ethane or ethylene.

A more particular feature of our invention resides in performing, while an operation is in progress, the transfer of only part of the products contained in a cell to the next cell, so not to break up the reaction equilibrium in the various cells. This allows continuous gas production without having to restart the reaction each time.

In a preferred mode of realization of this process, the product obtained at the end of the treatment in the last cell is recycled to the first enclosure in order to seed the latter with methane-producing bacteria.

More particularly, this process involves oxygenating the materials in the first cell, then—prior to transfer to the second cell—establishing an anaerobic atmosphere by injection of carbon dioxide, and possibly bringing to the other cells an additional volume of carbon dioxide and of hydrogen while maintaining a temperature between 35° and 45° C., preferably between 37.5° and 41° C., the recovery of methane taking place in these last cells.

BRIEF DESCRIPTION OF THE DRAWINGS

Our invention will now be described in detail with reference to the annexed diagrammatic drawing which shows, by way of a nonlimiting example, two embodiments of a typical plant for the realization of this process. In the drawing.

SPECIFIC DESCRIPTION

Figure 1:
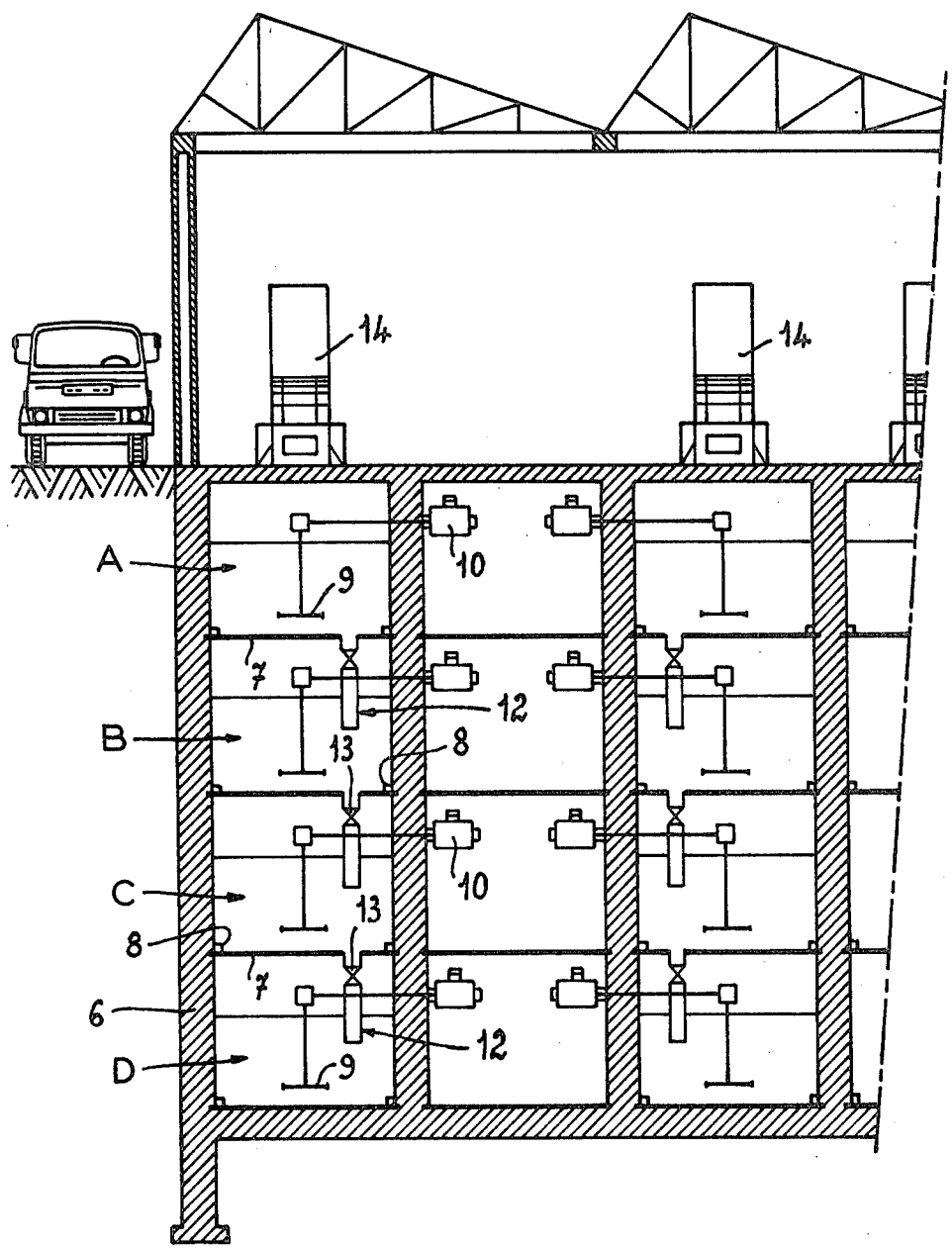
FIG. 1 is a highly diagrammatic sectional view of part of a major treatment plant.

Each treatment unit of the plant partially shown in the drawing includes four separate cells. Cell A allows the preparation and oxygenation of the sludge. Cell B insures prefermentation. Cell C allows the acceleration of fermentation producing carbonic gas and the beginning of methane fermentation. Cell D insures the enrichment of the produced gas with methane.

In the embodiment shown in FIG. 1, each cell has a width of approximately 3 meters, a height of 2.5 meters, and a length raning between 9 and 90 meters, this length depending upon the magnitude of the treatment center considered.

The cells are bounded longitudinally by reinforced concrete walls 6 of 60 cm thickness. The floors and ceilings separating the cells are made of hollow metal plates 7 inside which a temperature-controlling fluid is circulated.

Each floor supports adjacent the longitudinal edges of its cell, perforated tubes 8 which allow the delivery of constituents promoting the reaction, namely air, substratum, sustaining gas such as hydrogen and carbon dioxide, or hydrocarbons for the calorific enrichment of the gases, as the case may be.

Inside each cell we provide an agitator here shown to consist of a horizontal disk 9, set into rotary motion by an electric motor 10.

In the embodiment shown in FIG. 1, the four cells of a given unit are superposed. The cells communicate with one another by ducts 12 each provided with at least one valve 13.

These ducts allow the transfer by gravity of the sludge from an upper cell to a cell placed below. Upon their arrival at the treatment center, the various kinds of refuse are screened separate any metal parts present therein. The other constituents are comminuted in a crusher 14 and then fed to a cell A. This cell A is filled to a considerable height with liquids recovered from final cells D and brought back by a duct 15 which is equipped with a pump 16 (see FIGS. 2 and 3). Duct 15 leads from the bottom of a cell D to the top of a cell A. Refuse issuing from crusher 14 is added to these liquids.

Homogenization of the sludge is effected by the agitator disks 9. The sludge becomes extremely compact without, however, increasing in volume. From the outset of the mixing operation, air is injected through the distributing conduits 8 so as to effect the oxygenation of the mixture. After a certain reaction time, part of the sludge is transferred to cell B; prior to the transfer operation, however, cell A is placed in an anaerobic state by distribution of carbon dioxide through conduits 8.

Between cell A and cell B, duct 12 is provided with two valves 13 between which a filter 17 (see FIGS. 2 and 3) has been inserted. The two valves, preferably automated, open and close simultaneously.

Under the effect of pressure in cell A, the sludge proceeds to cell B through filter 17. To clean filter 17, it will only be required that the two valves 13 be in the closed position.

Cell B insures prefermentation which produces carbon dioxide. In order to accelerate this process, we may either increase the temperature of the mixture by motion of disks 9 or bring in additional gas through ducts 8, such as carbon dioxide or a mixture of hydrogen and carbon dioxide.

After a reaction time in this cell, the sludge is transferred to cell C. This transfer is effected in the same manner as that from cell A to cell B. In cell C the acceleration of the fermentation occurs which produces carbon dioxide and the beginning of methane fermentation. It is possible to accelerate the process by bringing in, as in the case of cell B, additional carbon dioxide and hydrogen, and by maintaining an optimal temperature of 41° C. for example.

After a certain reaction time, part of the sludge is transferred from cell C to a cell D. Cell D insures the enrichment of the resulting gas with methane. In that cell, the temperature is maintained between 35 and 45° C., advantageously between 37.5 ° and 41° C., the ideal temperature range in order to obtain an optimal production of methane.

This enrichment is obtained by injection of the gas output of cell B into cell C, and of the gas volume produced in cell C into cell D, by means of ducts 18 interconnecting the insides of two adjacent cells and by means of other ducts, not shown in the drawing, linking the interior of a cell with the distribution conduits 8 of the adjacent cell.

The gas volume produced in cell B contains 85% carbon dioxide and 15% methane, the gas volume produced in cell C contains 70% carbon dioxide and 30% methane, and the gas volume produced in final cell D contains 60% methane and 40% carbon dioxide. The injection of the gas output of cells B and C into cells C and D, respectively, via conduits B is particularly desirable since it allows an enrichment of the sludge by addition of a substratum and of methane-producing bacteria.

Naturally, valves are provided for controlling the distribution of the gas, both directly and indirectly through conduits 8.

The final yield will therefore be the sum of the gas outputs of the three cells B, C and D. The gas produced in the three cells is used as carrier gas.

To the extent that the gas production of cells B, C, and D fails to reach a sufficient volume of the order of 120 to 150 liters per hour and per m$^3$ of sludge, it is possible to inject industrial carbon dioxide in order to supplement it. This addition from outside may slightly lower the methane content. This, however, is of no importance since, at the exit of cell D, carbon dioxide is dissolved in a solution supersaturated with potash KOH. The crystals which remain at the bottom of the tanks are recovered in order to be introduced into cell A to maintain there a pH superior or equal to 7, this pH falling in the course of fermantation in cells B and C before rising again in cell D.

Figure 2:
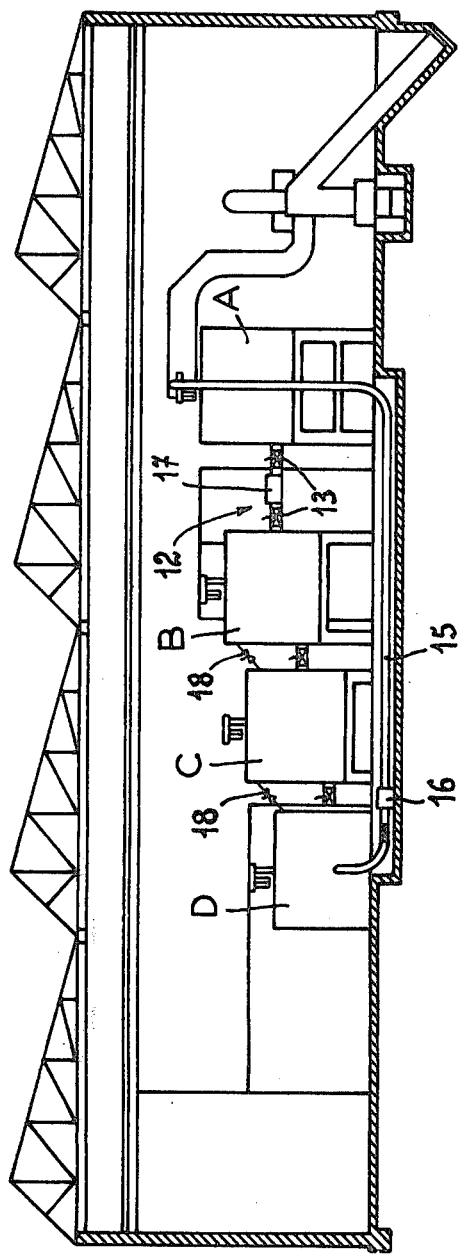
FIG. 2 is a sectional view of a minor transformation unit taken on the line 2—2 of FIG. 3.
Figure 3:
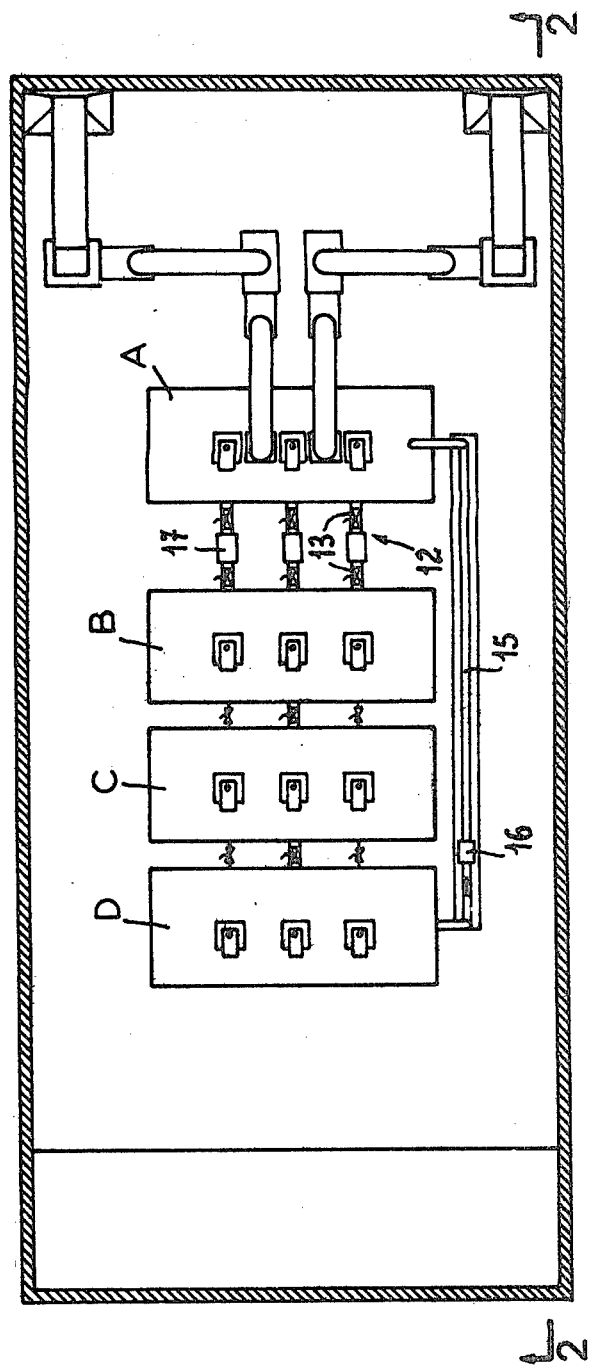
FIG. 3 is a top view of the unit shown FIG. 2.

In the modified assembly shown in FIGS. 2 and 3, the various cells A to D are not superimposed but simply laid out in stairway-like fashion, the important feature being that the sludge is still able to migrate by gravity from one cell to the next one below.

In addition to providing an economical source of energy, our process is advantageous in that there is no rejection of gas or sludge and therefore no atmospheric, stream, or water-table pollution.

It is also possible to recycle to cell A only part, for instance 90%, of the liquid obtained in cell D at the end of fermentation, the other part, i.e. the 10% remainder in the example considered, being seeded with previously isolated methane-producing bacteria. This bacteria-enriched fraction is then mixed with materials such as slime, brackish water, dead leaves, etc. in order to effect their controlled fermentation so as to obtain methane by means of an installation including several cells with specific functions as described above. Obviously, if we proceed in this manner, it is necessary to supply cell A with a new volume of sludge rich in organic materials corresponding to the unrecycled liquid volume in cell D in order to maintain the volume in cell A constant.

The treatment process in the cells would remain the same if the crushing of garbage were to take place, as previously indicated, at residential or industrial sites with the addition of recal matter and raw sewage.

We claim:

1. A process for converting organic wastes into industrial gases, comprising the steps of:

collecting and comminuting biodegradable waste material;

admixing the comminuted waste material in a first cell with a liquid containing methane-producing bacteria to form a fermentable sludge;

oxygenating said sludge in said first cell by injection of air with concurrent agitation;

thereafter establishing an anaerobic atmosphere around said sludge by introducing carbon dioxide into said first cell;

subsequently transferring the sludge from said first cell into a second cell for preformentation with predominant evolution of carbon dioxide;

thereafter transferring the sludge from said second cell into a final cell for fermentation with predominant evolution of methane; and extracting at least part of the liquid in the sludge of said final cell for recirculation to said first cell while recovering the methane therefrom.

2. A process as defined in claim 1 wherein the sludge preformented in said second cell is transferred to a third cell for the start of a methane-producing fermentation before being transferred to said final cell for further fermentation.

3. A process as defined in claim 2 wherein, at any given time, only a fraction of the sludge is transferred to said second, third and final cells from the immediately preceding cells for maintaining the reaction equilibrium in each preceding cell.

4. A process as defined in claim 2 wherein said first, second, third and final cells are disposed at successively lower levels, the transfer of the sludge from one cell to the next being effected by gravity.

5. A process as defined in claim 2 wherein the gas present in said final cell is passed through a liquor capable of dissolving a substantial part of the carbon dioxide accompanying the generated methane.

6. A process as defined in claim 5 wherein said liquor is a solution supersaturated with KOH.

7. A process as defined in claim 2 wherein the temperature in said second, third and final cells is maintained between substantially 35° and 45° C.

8. A process as defined in claim 7 wherein said temperature is maintained by controlled agitation of the sludge.

9. A process as defined in claim 7 wherein said temperature lies between 37.5° and 41° C.

10. A process as defined in claim 7 wherein said temperature is maintained at substantially 41° C. at least in said final cell.

11. A process as defined in claim 1 wherein the sludge in said first cell is maintained at a pH of not less than 7.

* * * * *